(12) United States Patent
Ogusu

(10) Patent No.: US 9,234,791 B2
(45) Date of Patent: Jan. 12, 2016

(54) LIGHT EMISSION DETECTION DEVICE HAVING A FLOW PATH FORMED BY A DEPRESSION OF A DETECTION SIDE SUBSTRATE AND METHOD OF MANUFACTURING THE SAME

(75) Inventor: Makoto Ogusu, Shimotsuke (JP)

(73) Assignee: Canon Kabushiki Kaisha, Tokyo (JP)

( * ) Notice: Subject to any disclaimer, the term of this patent is extended or adjusted under 35 U.S.C. 154(b) by 153 days.

(21) Appl. No.: 13/983,754

(22) PCT Filed: Jan. 25, 2012

(86) PCT No.: PCT/JP2012/052197
§ 371 (c)(1),
(2), (4) Date: Aug. 5, 2013

(87) PCT Pub. No.: WO2012/108303
PCT Pub. Date: Aug. 16, 2012

(65) Prior Publication Data
US 2013/0313417 A1   Nov. 28, 2013

(30) Foreign Application Priority Data
Feb. 7, 2011   (JP) .................. 2011-024018

(51) Int. Cl.
*H01J 5/02* (2006.01)
*G01J 1/42* (2006.01)
*B01L 3/00* (2006.01)
*G01N 21/03* (2006.01)
(Continued)

(52) U.S. Cl.
CPC .............. *G01J 1/42* (2013.01); *B01L 3/502707* (2013.01); *B29D 11/00* (2013.01); *G01N 21/0332* (2013.01); *G01N 21/05* (2013.01); *G01N 21/645* (2013.01); *B01L 2200/0689* (2013.01);
(Continued)

(58) Field of Classification Search
CPC ................ B01L 2300/0864; B01L 3/502746; B01L 2300/0867; B29D 11/00; G01J 1/42; G01J 5/024
USPC .............. 250/239, 573, 576, 214.1; 356/352, 356/136, 437, 445, 446; 422/82.05, 82.09, 422/82.11; 385/12, 14; 73/1.16, 53.04
See application file for complete search history.

(56) References Cited

U.S. PATENT DOCUMENTS 7,482,585 B2 *   1/2009   Sando et al. .................. 250/288

FOREIGN PATENT DOCUMENTS

JP   5-0240872 A   9/1993
JP   11-500602 A   1/1999
(Continued)

*Primary Examiner* — Que T Le
(74) *Attorney, Agent, or Firm* — Canon USA, Inc. IP Division

(57) ABSTRACT

A light emission detection device having a flow path from which light to be detected is emitted is provided. The device includes a detection-side substrate having a joining surface and a detection surface provided opposite the joining surface, the joining surface having a depression and a light-shielding film provided over an area excluding the depression, the depression forming the flow path, the detection surface transmitting the light emitted from the flow path; and a wiring-side substrate having a joining surface and a conductive pattern provided with a varying thickness on the joining surface, the joining surface of the wiring-side substrate joining the joining surface of the detection-side substrate. In the area over which the light-shielding film is provided, adhesive is provided with a thickness corresponding to the varying thickness of the conductive pattern and the detection-side substrate and the wiring-side substrate are closely joined to each other with the adhesive.

9 Claims, 4 Drawing Sheets

(51) Int. Cl.
  *G01N 21/05* (2006.01)
  *G01N 21/64* (2006.01)
  *B29D 11/00* (2006.01)

(52) U.S. Cl.
  CPC .. *B01L2300/0654* (2013.01); *B01L 2300/0816* (2013.01); *B01L 2300/0877* (2013.01); *B01L 2300/1827* (2013.01); *G01N 2021/0346* (2013.01); *G01N 2201/064* (2013.01)

(56) References Cited

FOREIGN PATENT DOCUMENTS

| | | |
|---|---|---|
| JP | 2002-286627 A | 10/2002 |
| JP | 2005-037368 A | 2/2005 |
| JP | 2006-078414 A | 3/2006 |
| JP | 2009-542207 A | 12/2009 |

* cited by examiner

LIGHT EMISSION DETECTION DEVICE HAVING A FLOW PATH FORMED BY A DEPRESSION OF A DETECTION SIDE SUBSTRATE AND METHOD OF MANUFACTURING THE SAME

TECHNICAL FIELD

The present invention relates to light emission detection devices having flow paths from which light to be detected is emitted, and to methods of manufacturing the same. In particular, the present invention relates to a fluorescence detection device to be used in genetic tests, protein tests, and the like, and to a method of manufacturing the same.

BACKGROUND ART

In earlier sample tests, the amounts of reagents required in chemical analysis, formulation of reagent, chemical synthesis, detection of reaction, and so forth are in milliliter to microliter order. In such test-tube-scale tests, microscopic reaction sites are formed by application of technologies such as a lithographic process and a thick-film process. Thus, nanoliter-order tests have recently become practicable. A technology called micro total analysis system (μ-TAS) in which such microscopic reaction sites are utilized is applied to the fields of, for example, medical tests and diagnosis including genetic tests, chromosome tests, and cell tests, and biotechnologies including tests for very small amounts of substances contained in the environment, investigations of environments in which crops and the like are grown, and genetic tests for crops. In earlier test technologies, reagents are handled basically relying on the skill of testing technicians. The procedure of such a test, however, is complicated, and expertise in the operation of testing instruments is necessary. In contrast, μ-TAS is attracting attention as a technology that produces great advantages in terms of automation, high speed, high accuracy, low costs, quickness, reduced impact on the environment, and so forth.

To conduct a test with a flow path device employing the μ-TAS technology while utilizing the fluorescence intensity, noise fluorescence emitted from any matter other than the sample liquid needs to be suppressed because the intensity of fluorescence from a nanoliter-order sample is weak. To suppress noise fluorescence, PTL 1 discloses a flow path device 110 (see FIGS. 7 and 8) in which light-shielding portions 116 are provided on a substrate 111 having a flow path 113 in such manner as to extend along the flow path. Thus, fluorescence emitted from the substrate 111 is blocked with the light-shielding portions 116.

FIGS. 7 and 8 illustrate the flow path device 110 disclosed by PTL 1. In PTL 1, a joining method in which no adhesive is used, such as hot pressing, is employed. In such a joining method, joining surfaces 111a of the substrates 111 and 112 to be joined to each other need to be completely flat, as illustrated in sectional view in FIG. 8, or the substrates 111 and 112 need to be sufficiently deformable in response to an external action performed when the substrates 111 and 112 are joined (for example, the substrates 111 and 112 need to be made of resin). That is, if the substrates 111 and 112 are made of a brittle material such as quartz, a step of flattening the joining surfaces 111a of the substrates 111 and 112 is necessary after the light-shielding portions 116 are formed. For example, after the light-shielding portions 116 are formed on the substrate 111, another material may be provided thereover with a larger thickness than the light-shielding portions 116 and the surface of the material may be ground. For another example, portions of the substrate 111 may be removed in advance to a depth corresponding to the thickness of the light-shielding portions 116, and, after the light-shielding portions 116 are formed, the resulting body may be ground so as to remove unnecessary part and flatten the surface. In either way, a flattening step is necessary. Such a method is disadvantageously troublesome and costly.

Meanwhile, PTL 2 discloses a flow path device that is manufactured using adhesive and includes a light-shielding layer. In PTL 2, no specific method of manufacturing the flow path device is disclosed, and whether or not any wiring patterns and so forth are included in the device is unknown.

CITATION LIST

Patent Literature

PTL 1 Japanese Patent Laid-Open No. 2006-078414
PTL 2 Japanese Patent Laid-Open No. 2002-286627
PTL 3 PCT Japanese Translation Patent Publication No. 2009-542207

SUMMARY OF INVENTION

Technical Problem

The present invention provides a light emission detection device in which substrates having irregular surfaces are stably joined to each other while unwanted light emission is prevented from reaching a detecting unit.

The present invention also provides a method of manufacturing the above light emission detection device.

According to a first aspect of the present invention, there is provided a light emission detection device having a flow path from which light to be detected is emitted. The device includes a detection-side substrate having a joining surface and a detection surface provided opposite the joining surface, the joining surface having a depression and a light-shielding film provided over an area excluding the depression, the depression forming the flow path, the detection surface transmitting the light emitted from the flow path; and a wiring-side substrate having a joining surface and a conductive pattern provided with a varying thickness on the joining surface, the joining surface of the wiring-side substrate joining the joining surface of the detection-side substrate. In the area over which the light-shielding film is provided, adhesive is provided with a thickness corresponding to the varying thickness of the conductive pattern and the detection-side substrate and the wiring-side substrate are joined to each other with the adhesive.

According to a second aspect of the present invention, there is provided a method of manufacturing a light emission detection device. The method includes forming a light-shielding film on a light-transmissive substrate, patterning the light-shielding film on the substrate in such a manner as to correspond to a flow path pattern, etching the substrate by using the light-shielding film as a mask such that a surface of the substrate comes to have a depression while an area excluding the depression remains covered with the light-shielding film, applying adhesive onto the area of the substrate excluding the depression, and joining the substrate to a wiring-side substrate with the adhesive, the wiring-side substrate having a conductive pattern provided thereon with a varying thickness.

Advantageous Effects of Invention

According to the above aspects of the present invention, the substrates, which have irregular surfaces, can be joined to each other without a troublesome flattening step. Moreover, if the above light emission detection device is applied to an apparatus configured to observe light emission with a light emitting/receiving device, unwanted fluorescence emission can be prevented from being generated and reaching a detecting unit.

DESCRIPTION OF EMBODIMENTS

Embodiments of the present invention will now be described in detail with reference to the accompanying drawings.

A light emission detection device according to the present invention includes a flow path provided by joining two substrates. Light emitted from the flow path of the device is to be detected.

The light emission detection device according to the present invention can be used as a medical test device intended for medical tests and diagnosis. A medical test device is a general device, represented by μ-TAS, to be used for purposes of medical tests and diagnosis. Exemplary medical test devices include a deoxyribonucleic-acid (DNA) chip, a lab-on-a-chip, a microarray, a protein chip, and the like.

The light emission detection device according to the present invention, which includes a flow path into which a fluid is to be introduced, may further include spaces, such as a reaction site and a storage space, into which the fluid is to be introduced. The device may include a substrate having a groove forming a flow path and so forth, specifically, a plurality of substrates that are joined to each other and in combination form spaces, including a flow path, therebetween. Examples of the fluid include a liquid containing a reagent or a sample, basically. Moreover, gas such as air may be used as a carrier, or a semisolid substance having fluidity may be used.

FIGS. 1A to 1E illustrate a light emission detection device 20 according to an embodiment of the present invention.

Figure 1A:
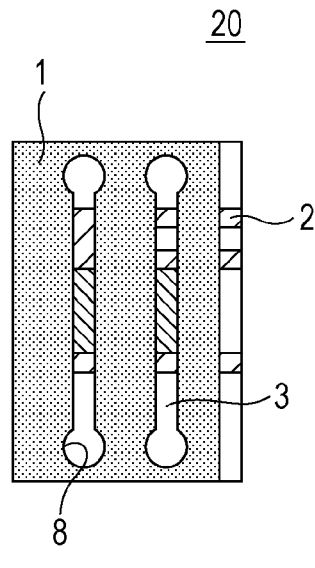
FIG. 1A is a top view of a light emission detection device according to an embodiment of the present invention.
Figure 1B:
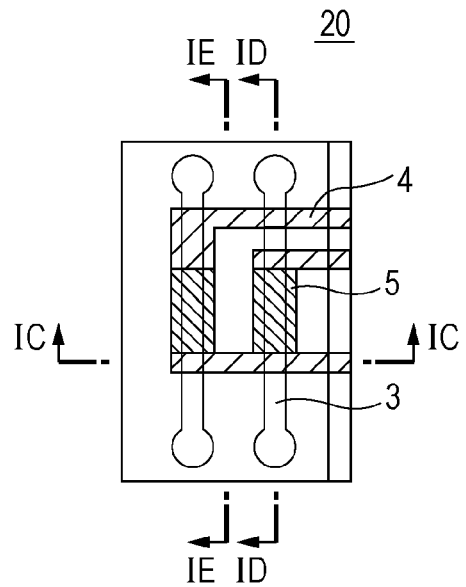
FIG. 1B illustrates an arrangement of patterns provided in the light emission detection device.
Figure 1C:
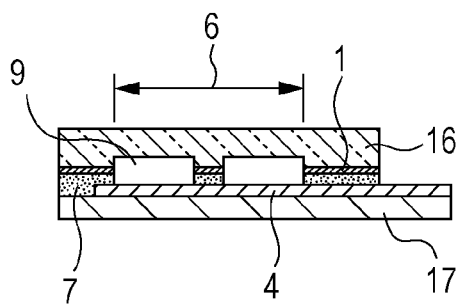
FIG. 1C is a sectional view of the light emission detection device taken in a direction orthogonal to flow paths.
Figure 1D:
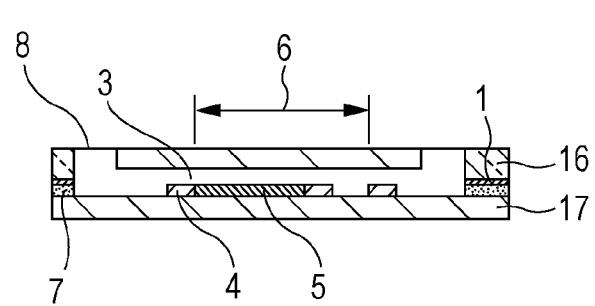
FIG. 1D is another sectional view of the light emission detection device taken along one of the flow paths.
Figure 1E:
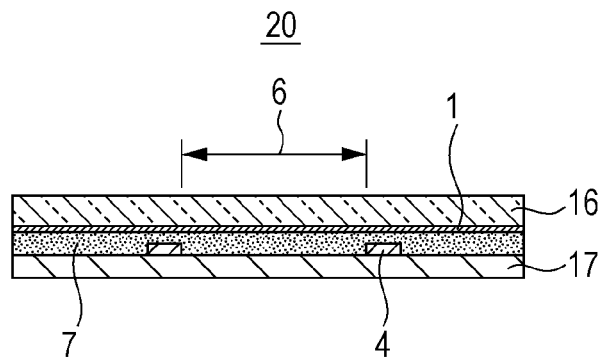
FIG. 1E is yet another sectional view of the light emission detection device taken along a line extending between the flow paths.

FIG. 1A is a top view of the light emission detection device 20. FIG. 1B is another top view of the light emission detection device 20 seen through a light-shielding film 1 thereof and illustrating the arrangement of patterns included therein. FIGS. 1C to 1E are sectional views of the light emission detection device 20. FIG. 1C illustrates flow paths 3 in a section taken in a direction orthogonal to the flow paths 3. FIG. 1D illustrates one of the flow paths 3 in a section taken therealong. FIG. 1E illustrates a section taken along a virtual line extending between the flow paths 3.

Referring to FIGS. 1A to 1E, the light emission detection device 20 includes the light-shielding film 1, pads 2 that provide electric connections to an external device, the flow paths 3, a conductive pattern 4, heater members 5, a detection surface 6, adhesive 7, and introduction/discharge ports 8.

A detection-side substrate 16 has a joining surface and the detection surface 6 provided opposite the joining surface. The joining surface has depressions 9 and the light-shielding film 1. The depressions 9 form the flow paths 3. The light-shielding film 1 is provided over an area excluding the depressions 9. Light emitted from the flow paths 3 is transmitted through the detection surface 6 so as to be detected.

A wiring-side substrate 17 has a joining surface and a conductive pattern 4 provided with a varying thickness on the joining surface. The joining surface of the wiring-side substrate 17 joins the joining surface of the detection-side substrate 16.

The detection-side substrate 16 and the wiring-side substrate 17 are thus joined together. In the area over which the light-shielding film 1 is provided, the adhesive 7 is provided with a thickness corresponding to the varying thickness of the conductive pattern 4, whereby the detection-side substrate 16 and the wiring-side substrate 17 are closely joined to each other with the adhesive 7.

As illustrated in top view in FIGS. 1A and 1B, the light emission detection device 20 includes two flow paths 3, each of which has the introduction/discharge ports 8, through which a reagent is introduced into and discharged from the flow path 3. The heater members 5 are provided in central portions of the respective flow paths 3. FIG. 1B illustrates the positional relationship among the heater members 5, the conductive pattern 4, and the flow paths 3 seen through the light-shielding film 1.

Referring to the sectional view illustrated in FIG. 1D taken along one of the flow paths 3, two ends of each of the heater members 5 are connected to the conductive pattern 4. The heater members 5 are provided in part of the respective flow paths 3.

The conductive pattern 4 connected to the heater members 5 extends across the flow paths 3 and has the pads 2. The pads 2 provide electric conduction and are provided on a portion of the wiring-side substrate 17 that is not covered with the detection-side substrate 16.

The detection-side substrate 16, defining the upper side of the flow paths 3, is transparent so that fluorescence emitted from the flow paths 3 is transmitted therethrough to the outside. A portion of the detection-side substrate 16 through which the fluorescence is emitted to the outside is herein referred to as the detection surface 6. A side of the detection surface 6 nearer to the heater members 5 and the conductive pattern 4 is shielded from light and does not exert its function as the detection surface 6. Hence, the detection surface 6 is positioned across the flow paths 3 from the member having the heater members 5 and the conductive pattern 4.

In the embodiment, the heater members 5 and the conductive pattern 4 are provided on a flat surface of the wiring-side substrate 17, not on the detection-side substrate 16 having the depressions 9 forming the flow paths 3. The wiring-side substrate 17 having the flat surface is easy to provide metal patterns thereon.

Thus, light is emitted and received through the detection surface 6 of the detection-side substrate 16 having the depressions 9 forming the flow paths 3.

As described above, the light emission detection device 20 according to the embodiment of the present invention is obtained by joining together the detection-side substrate 16, which is transparent and has the depressions 9, and the wiring-side substrate 17, which has a flat surface and is provided with the heater members 5 and the conductive pattern 4.

The detection-side substrate 16 and the wiring-side substrate 17 may be made of either the same material or different materials.

The detection-side substrate 16 and the wiring-side substrate 17 may be both made of quartz. Quartz is superior in terms of thermal and chemical stability.

Any materials other than quartz are also acceptable, as long as they are light-transmissive or have characteristics equivalent thereto. For example, Pyrex (a registered trademark and a brand name) and BOROFLOAT (a registered trademark and a brand name) can be named.

As illustrated in FIGS. 1C and 1D, the heater members 5 and the conductive pattern 4, which are metal patterns, have finite thicknesses.

If the two substrates 16 and 17 are closely joined to each other while there are differences in the thickness of the metal patterns, such thickness differences may produce gaps in walls defining the flow paths 3.

If the reagent leaks out of (or flows into) the flow paths 3 through such gaps, the fluid in the flow paths 3 may be contaminated. In a system in which the fluid is moved in the flow paths 3 by utilizing the pressure, the movement may not be controlled as intended. Therefore, such a situation needs to be avoided.

In the embodiment of the present invention, the substrates 16 and 17 are joined to each other with the adhesive 7. The adhesive 7 fills gaps including those described above. Therefore, even if the substrates 16 and 17 have irregular surfaces, the substrates 16 and 17 can be joined together with no gaps. Furthermore, the detection-side substrate 16 having the depressions 9 forming the flow paths 3 is provided with the light-shielding film 1 on the joining surface thereof excluding the area corresponding to the flow paths 3. The light-shielding film 1 is provided between the detection surface 6 and the adhesive 7. Therefore, even if the adhesive 7 emits fluorescence, fluorescence noise from the adhesive 7 is blocked. Thus, a good light emission detection device is provided.

The light-shielding film 1 according to the embodiment of the present invention is not limited to a specific film, as long as the film can block light and is easy to join with adhesive. In particular, a material that is resistant to selective etching to be performed on the detection-side substrate 16 in a process subsequent to the formation of the light-shielding film 1 may be used. In general, a metal film is suitable for the light-shielding film 1. If the detection-side substrate 16 is made of quartz, a chromium metal film may be used as the light-shielding film 1, as described below.

In the embodiment, a reagent is introduced into the flow paths 3, which are fine channels, and is then continuously heated. A reaction of changes in the amount of fluorescence from the reagent caused by the heating is utilized in a medical test.

The heater members 5 according to the embodiment of the present invention can be used as heaters that continuously heat the fluid containing the reagent and flowing in the flow paths 3. Since the heater members 5 that generate heat are provided close to the flow paths 3 into which the fluid is introduced, quick and stable heating is realized.

Moreover, if the heater members 5 that generate heat are made of a material whose temperature dependence is known, such as platinum, and the resistance of the material is measured, the temperature of any heat generating body can also be found from relevant physical constants.

Thus, at what temperature of the reagent the measured amount of fluorescence is emitted can be found.

If the heater members 5 are provided directly below the flow paths 3, more accurate temperature measurement is realized.

To form the heater members 5 made of platinum and to provide assured energy supply to and electric contact with the platinum heater members 5 while accurate temperature measurement and control is realized as described above, the conductive pattern 4 may be made of gold. Ends of such a gold pattern may be continuous with the pads 2 provided on a portion of the wiring-side substrate 17 that is not covered with the detection-side substrate 16.

Method of Manufacturing Light Emission Detection Device

A method of manufacturing the light emission detection device 20 according to the embodiment of the present invention will now be described.

While the method will be described with reference to sectional views of a single chip, a plurality of chips may be manufactured at a time in units of wafers, practically. Individual light emission detection devices 20 are obtained by cutting each wafer into pieces in the last step.

Figure 2:
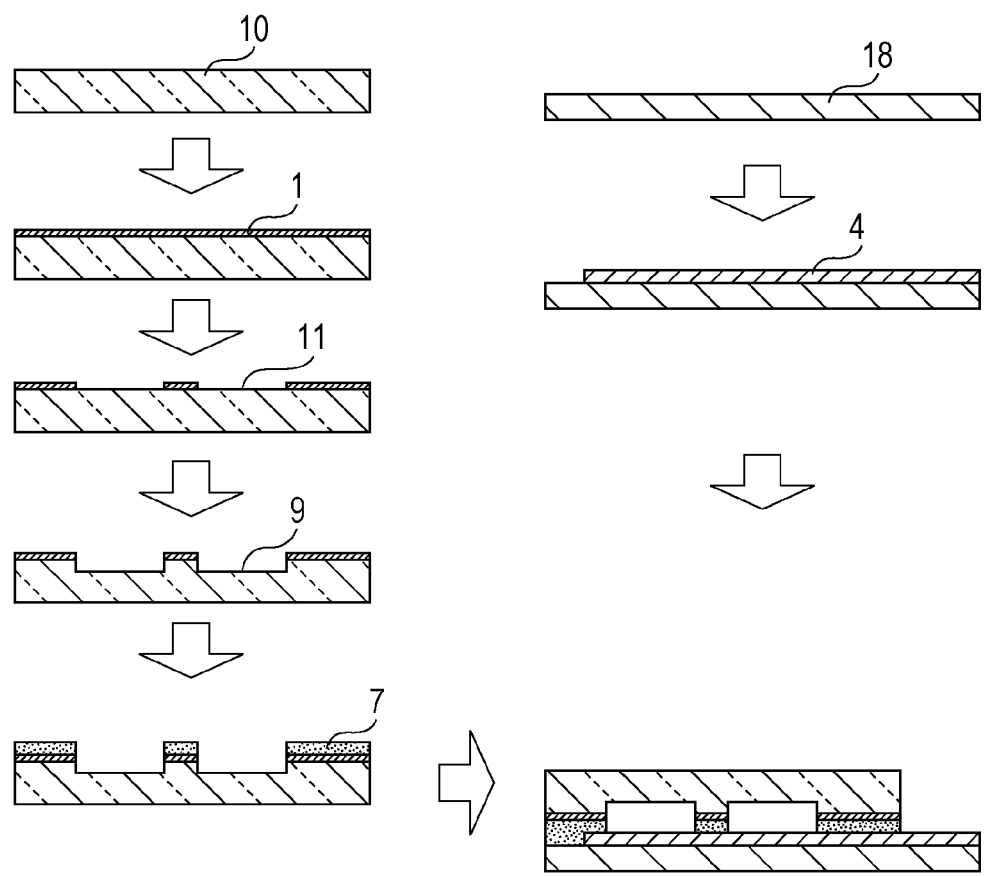
FIG. 2 illustrates a method of manufacturing the light emission detection device according to the embodiment of the present invention.

FIG. 2 illustrates the method of manufacturing the light emission detection device 20 according to the embodiment of the present invention. First, a light-shielding film 1 is formed on a quartz substrate 10, in which depressions 9 that are to become flow paths 3 are formed later. Part of the light-shielding film 1 is photolithographically removed such that an opening pattern 11 corresponding to the flow paths 3 is formed. The light-shielding film 1 may be made of any material, as long as the material is resistant to selective dry etching to be performed on the quartz substrate 10 in a subsequent process. In general, a metal film is suitable for the light-shielding film 1. The quartz substrate 10 provided with the light-shielding film 1 having the opening pattern 11 is dry etched, whereby depressions 9 are provided. Subsequently, holes that are to become introduction/discharge ports 8 and openings through which contacts with the pads 2 are to be provided when a final product as a light emission detection device 20 is obtained are provided in the quartz substrate 10 (not illustrated).

Meanwhile, heater members 5 (not illustrated in FIG. 2) and a conductive pattern 4 are formed on another substrate 18. After the completion of the above processing of the two substrates 10 and 18, adhesive 7 is applied onto the quartz substrate 10 having the depressions 9 that are to become flow paths 3. Considering the simplicity of the manufacturing process, the adhesive 7 may be applied onto the quartz substrate 10 having the depressions 9. This is because the depressions 9 that are to become flow paths 3 determine the area of the joining surface and the area of the non-joining surface.

The adhesive 7 absorbs surface irregularities produced with the presence of the conductive pattern 4, and thus makes the two substrates 10 and 18, i.e., the substrates 16 and 17, closely joined to each other.

That is, since the adhesive 7 is provided into gaps produced by differences in the distance between the two substrates 16 and 17 due to the surface irregularities, the substrates 16 and 17 are closely joined to each other, not allowing the fluid to leak out through the gaps.

To realize more assured and close joining of the substrates 16 and 17, the adhesive 7 may be provided on the detection-side substrate 16 with a thickness varying in accordance with the surface irregularities produced by the conductive pattern 4.

Alternatively, the adhesive 7 may be provided with a uniform thickness on the detection-side substrate 16 and the substrates 16 and 17 may be then joined together while a pressure is applied thereto such that the adhesive 7 is moved between the substrates 16 and 17 and gaps produced by surface irregularities are filled with the adhesive 7. Thus, the substrates 16 and 17 may be closely joined to each other.

The final thickness of the adhesive 7 is set appropriately in accordance with the extent of the irregularities.

For example, relative to a largest difference A in the height of surface irregularities, the adhesive 7 may have a largest thickness of twice the largest difference A or greater (2·A or greater) and smaller than a thousand times the largest difference A (smaller than 1000·A), or preferably smaller than a hundred times the largest difference A. If the largest thickness of the adhesive 7 is smaller than twice the largest difference A, the adhesion between the substrates 16 and 17 may be insufficient. If the largest thickness of the adhesive 7 is greater than or equal to a thousand times the largest difference A, the adhesive 7 may flow out into the flow paths 3 when the substrates 16 and 17 are joined together, and the detection of fluorescence may be affected.

The thickness of the adhesive 7 is appropriately set in accordance with the intended depth of the flow paths 3. For example, the smallest thickness of the adhesive 7 is preferably 0.1 μm or greater, or more preferably 1 μm or greater. The largest thickness of the adhesive 7 is preferably 1.1 μm to 2.0 mm.

The adhesive 7 may be of any kind, as long as it does not allow leakage of fluid and does not affect the fluid provided in the flow paths 3.

For example, any of the following can be used: epoxy resin adhesive, urethane resin adhesive, unsaturated polyester resin adhesive, phenolic resin adhesive, acrylic resin adhesive, styrene resin adhesive, melamine resin adhesive, and the like.

If any heater members are provided as in the embodiment, a material not denaturalized with heat up to 100° C. is selected as the adhesive 7. If any aqueous solution is fed into the flow paths 3, a material whose eluate does not substantially affect the reaction occurring in the flow paths 3 and whose amount of elution is small is selected as the adhesive 7.

After the adhesive 7 is provided, the substrates 16 and 17, which are in the form of wafers, are joined together while the relative positions thereof are adjusted with reference to alignment marks (not illustrated). After the joining, the resulting body is cut into pieces, whereby light emission detection devices 20 are obtained.

According to the embodiment, dry etching is performable using the light-shielding film 1 as an etching mask. Even after the flow paths 3 have been formed, the light-shielding film 1 as the etching mask remains with the opening pattern 11 provided therein and accurately matching the pattern of the flow paths 3. Thus, the light-shielding film 1 can be provided in such a manner as to extend to the edges of the flow paths 3. Accordingly, the adhesive 7 can be spread to the edges of the flow paths 3. With the adhesive 7 spread to the edges of the flow paths 3, unwanted gaps are not produced in the walls defining the flow paths 3.

Figure 3:
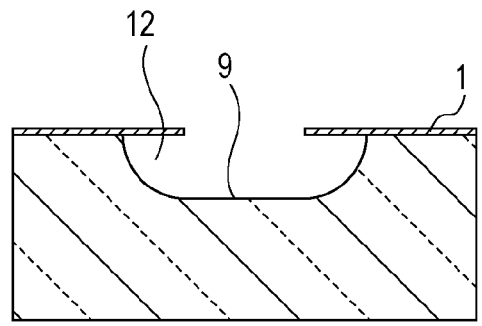
FIG. 3 illustrates an undercut portion produced in wet etching.

The depressions 9 that are to become the flow paths 3 may be provided by wet etching as illustrated in FIG. 3. In wet etching, the material is etched isotropically. Therefore, undercut portions 12 are produced below the edges of the light-shielding film 1, which defines the etching pattern.

If part of the light-shielding film 1 that has lost the base falls off and thus produces particles, failure may occur. To avoid such a situation, the part of the light-shielding film 1 that has lost the base may be removed by applying ultrasonic waves thereto.

In such a manner also, the pattern of remaining part of the light-shielding film 1 matches the pattern of the flow paths 3. In this case, the material of the substrate 10 is not limited to quartz, as long as the material is wet-etchable.

By such a wet etching method, the etching process is performable on a batch basis, not on a wafer basis as in the dry etching method. Consequently, the productivity is improved. The light-shielding film 1 used as an etching mask may be a chromium film. A chromium film as an etching mask exhibits good resistance to wet etching. Therefore, the quartz substrate 10 can be etched to a maximum depth of 50 μm.

Figure 4:
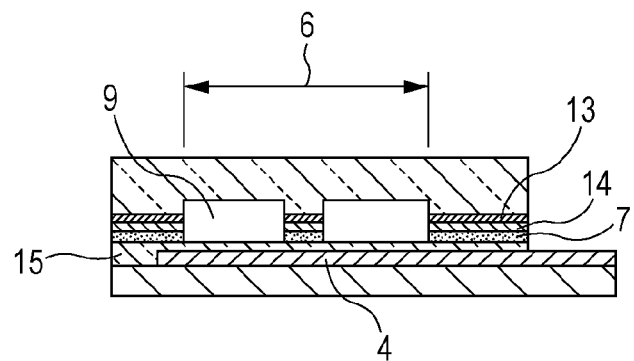
FIG. 4 illustrates a light emission detection device according to another embodiment of the present invention.

As in another configuration illustrated in FIG. 4, a metal oxide film 14 may be provided on a light-shielding film 13. With the metal oxide film 14 provided on a surface that is to be in contact with the adhesive 7, the adhesion is enhanced and a more stable light emission detection device is provided.

Furthermore, another metal oxide film 15 may be provided over the heater members 5 and the conductive pattern 4. Thus, the possibility that metal films, i.e., the heater member 5 and the conductive pattern 4, may cause electrolysis is eliminated, and testing operations and control operations are facilitated.

Figure 5:
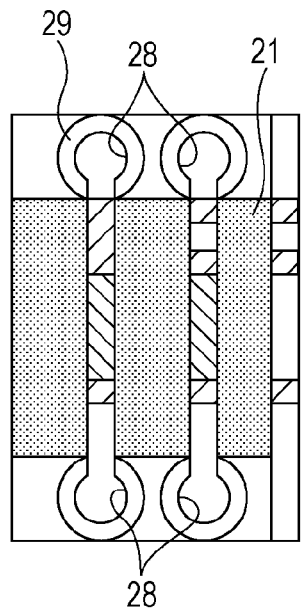
FIG. 5 illustrates a light emission detection device according to yet another embodiment of the present invention.

As in yet another configuration illustrated in FIG. 5, a light-shielding film 21 may be formed in such a manner as not to extend over and around introduction/discharge ports 28. Furthermore, as in yet another configuration illustrated in FIG. 6, an interface module 30 may be joined to the light emission detection device 20 with a surface adhesion layer 29 interposed therebetween.

The interface module 30 has a window 31, openings 32 and 33, and flow paths 34. Fluorescence emitted through the detection surface 6 is observed through the window 31. The fluid is introduced into the flow paths 3, is subjected to suction, and is discharged from the flow paths 3 through the openings 32 and 33. The flow paths 34 are connected to the respective introduction/discharge ports 28. The interface module 30 facilitates the connection to an external device such as a pipette and a syringe. The openings 32 and 33 of the interface module 30 facilitate the supplying of fluid and the movement of fluid in the light emission detection device 20.

The interface module 30 does not need to include heater members and conductive patterns and is not affected by heat. Therefore, the interface module 30 can be made of a relatively inexpensive resin.

If the interface module 30 is made of resin, however, the transmissivity of the interface module 30 with respect to ultraviolet light is not expected to be good. In this respect, the light-shielding film 21 is provided in such a manner as not to extend over and around the introduction/discharge ports 28 as described above so that ultraviolet light can be applied to the surface adhesion layer 29. Thus, an ultraviolet-curable resin can be used as the surface adhesion layer 29.

Detection Method Using Light Emission Detection Device

The light emission detection device 20 according to the embodiment of the present invention is applicable to detection of light emission performed by utilizing a phenomenon that a substance, to be provided in the flow paths 3, emits light at the occurrence of a biochemical reaction, and in particular to a method in which nucleic acid multiplied by polymerase chain reaction (PCR) is analyzed by utilizing the fluorescence. Specific devices of, for example, detecting the fluorescence and controlling the fluid in the flow paths 3 are available through publicly known techniques. For example, a system employing a light emission detection device is disclosed by PTL 3.

EXAMPLES

Examples of the present invention will now be described.

Example 1

In Example 1, a light emission detection device 20 the same as the one illustrated in FIGS. 1A to 1E was manufactured. Two flow paths 3 each having introduction/discharge ports 8 through which a reagent is introduced into and discharged from the flow path 3 were formed on a detection-side substrate 16. Heater members 5 made of platinum were formed on portions of a wiring-side substrate 17 corresponding to central portions of the respective flow paths 3.

Specifically, a platinum pattern 5 and a gold pattern 4 were formed on a quartz substrate 18, which was to become the wiring-side substrate 17, by using a deposition apparatus such that the patterns 5 and 4 and the flow paths 3 were arranged as illustrated in FIG. 1B. The gold pattern 4, which was connected to the platinum pattern 5, was made to extend across the flow paths 3. Pads 2 that were to provide electric conduction were formed on a portion of the substrate 18 that was not to be covered with a detection-side substrate 16. The thickness of the gold pattern 4 was about 0.4 μm.

The detection-side substrate 16 was manufactured by the method illustrated in FIG. 2. First, a light-shielding film 1 made of chromium metal was formed on a quartz substrate 10 by sputtering. Subsequently, part of the light-shielding film 1 was photolithographically removed such that an opening pattern 11 corresponding to the flow paths 3 was formed.

The quartz substrate 10 provided with the light-shielding film 1 having the opening pattern 11 was dry etched, whereby depressions 9 each having a depth of 16 μm were provided. Subsequently, holes that were to become introduction/discharge ports 8 and openings through which contacts with the pads 2 were to be provided when a final product as a light emission detection device 20 was obtained were provided.

Subsequently, resin adhesive 7 (SB bonding film of Yamanaka Semiconductor Co., Ltd.) was applied onto the quartz substrate 10 having the depressions 9, i.e., the detection-side substrate 16.

After the application of the adhesive 7, the substrates 16 and 17 in the form of wafers were joined together while the relative positions thereof were adjusted with reference to alignment marks (not illustrated). After the joining, the resulting body was cut into pieces, whereby light emission detection devices 20 were obtained.

When a liquid was fed into the flow paths 3 of the finished device with a pump, no leakage of the liquid and so forth occurred and good liquid feeding was realized.

When the thickness of the adhesive 7 provided between the two substrates 16 and 17 was measured, the thickness in a region where the conductive pattern 4 was provided was the smallest value of 4.0 μm, and the thickness in a region where the conductive pattern 4 was not present was 4.4 μm.

When light was applied to the flow paths 3 and light emitted through the detection surface 6 was observed, no emission of fluorescence from the adhesive 7 was observed.

Example 2

In Example 2, wet etching, instead of dry etching performed in Example 1, was performed on a quartz substrate 10.

A light-shielding film 1 made of chromium metal was first formed on the quartz substrate 10, as in Example 1, by using a deposition apparatus.

Subsequently, depressions 9 that were to become flow paths 3 were provided in the quartz substrate 10 by wet etching. In wet etching, the material is etched isotropically. Therefore, undercut portions 12 (see FIG. 3) were produced below the edges of the chromium-metal light-shielding film 1 defining the etching pattern. To avoid a situation where part of the chromium-metal light-shielding film 1 that had lost the base might fall off and produce particles, the part of the chromium-metal light-shielding film 1 that had lost the base was removed by applying ultrasonic waves thereto.

In Example 2 also, the pattern of remaining part of the light-shielding film 1 matched the pattern of the flow paths 3.

In Example 2 also, heater members 5 and a conductive pattern 4 were provided on a flat substrate 18 that had not been subjected to the above process. Therefore, the quartz substrate 10 in which the depressions 9 were provided needed to be transparent to the wavelength of light to be emitted from and applied to the emission detecting device 20.

According to Example 2, the etching process was performed on a batch basis, not on a wafer basis as in the dry etching method. Consequently, the productivity was improved. Furthermore, the light-shielding film 1 used as an etching mask was a chromium film, which exhibited good resistance to wet etching. Therefore, the quartz substrate 10 was able to be etched to a maximum depth of 50 μm. Furthermore, with the application of ultrasonic waves to the light-shielding film 1 after the wet etching, part of the chromium light-shielding film 1 extending above the undercut portions 12 was able to be removed selectively.

Example 3

In Example 3, as illustrated in FIG. 4, a chromium oxide film 14 was formed on a chromium light-shielding film 13, and a silicon dioxide film 15 was formed over metal patterns, i.e., a platinum pattern 5 and a gold pattern 4. The other members were formed in the same manner as in Example 1.

According to Example 3, with the oxide film 14 provided on a surface that was to be in contact with the adhesive 7, the adhesion was enhanced and a more stable light emission detection device was provided. Furthermore, when two electrodes were provided at different positions in one of the flow paths 3 and a potential difference was produced between the electrodes, the testing work was able to be performed at other points without the occurrence of electrolysis of the sample liquid and so forth.

Example 4

Figure 6:
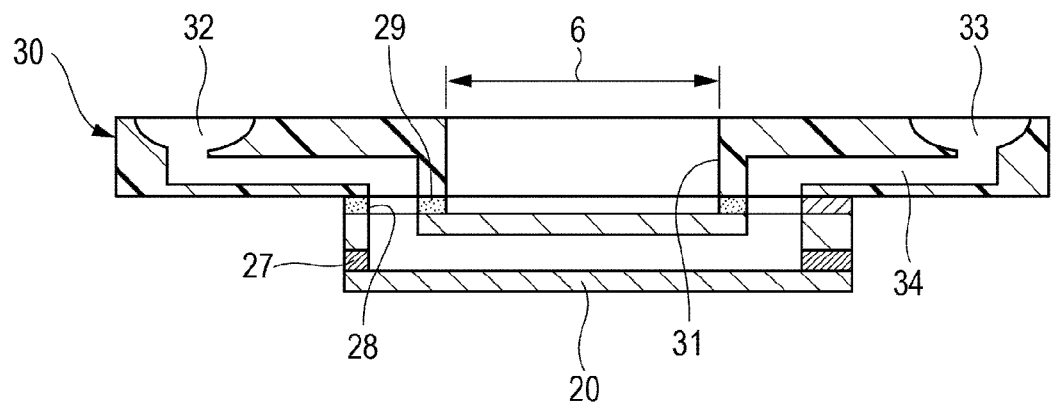
FIG. 6 illustrates a light emission detection device according to yet another embodiment of the present invention.
Figure 7:
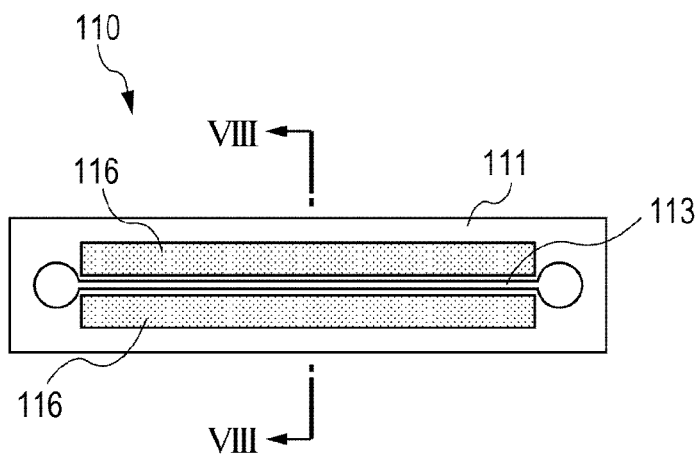
FIG. 7 illustrates a related-art flow path device.
Figure 8:
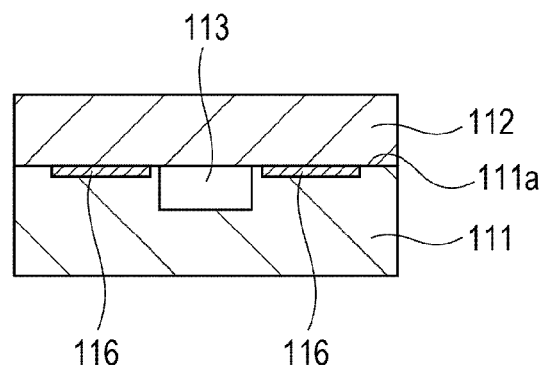
FIG. 8 is a sectional view of the related-art flow path device.

In Example 4, as illustrated in FIG. 5, a chromium light-shielding film 21 was formed in such a manner as not to extend over and around the introduction/discharge ports 28. Furthermore, as illustrated in FIG. 6, an interface module 30 made of resin was joined to the light emission detection device 20 with a surface adhesion layer 29 interposed therebetween. The interface module 30 had a window 31 as a space through which fluorescence emitted through the detection surface 6 was to be observed. The interface module 30 also had openings 32 and 33, through which liquid was to be introduced, and flow paths 34.

The light emission detection device 20 and the interface module 30 were joined to each other with ultraviolet-curable adhesive 29. The interface module 30 made of resin was not expected to have good transmissivity to ultraviolet light. Therefore, the adhesive 29 was cured by applying ultraviolet light to the adhesive 29 from the side of the light emission detection device 20. The light-shielding film 21 of the light emission detection device 20 was not made to extend over and around the introduction/discharge ports 28. Therefore, good adhesion was realized.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-024018, filed Feb. 7, 2011, which is hereby incorporated by reference herein in its entirety.

The invention claimed is:

1. A light emission detection device having a flow path from which light to be detected is emitted, the device comprising:
    a detection-side substrate having a joining surface and a detection surface provided opposite the joining surface, the joining surface having a depression and a light-shielding film provided over an area excluding the depression, the depression forming the flow path, the detection surface transmitting the light emitted from the flow path; and
    a wiring-side substrate having a joining surface and a conductive pattern provided with a varying thickness on the joining surface, the joining surface of the wiring-side substrate joining the joining surface of the detection-side substrate,
    wherein, in the area over which the light-shielding film is provided, adhesive is provided with a thickness corresponding to the varying thickness of the conductive pattern and the detection-side substrate and the wiring-side substrate are joined to each other with the adhesive.

2. The light emission detection device according to claim 1, wherein a heater member is provided in an area of the wiring-side substrate that defines the flow path.

3. The light emission detection device according to claim 2, wherein a longitudinal direction of the heater member corresponds to a direction in which the flow path extends.

4. The light emission detection device according to claim 1, wherein, at least in the area in which the adhesive is provided, an insulating film is provided over the conductive pattern.

5. The light emission detection device according to claim 1, wherein the light emission detection device is provided with an interface module including connection portions connected to an inlet and an outlet of the flow path of the light emission detection device, flow paths connected to the respective connection portions, and openings communicating with the respective flow paths of the interface module, the interface module being joined at the connection portions thereof to the light emission detection device with adhesive.

6. The light emission detection device according to claim 5, wherein areas of the light emission detection device over and around the inlet and the outlet of the flow path are free of the light-shielding film.

7. A method of manufacturing a light emission detection device, comprising:
    forming a light-shielding film on a light-transmissive substrate;
    patterning the light-shielding film on the substrate in such a manner as to correspond to a flow path pattern;
    etching the substrate by using the light-shielding film as a mask such that a surface of the substrate comes to have a depression while an area excluding the depression remains covered with the light-shielding film;
    applying adhesive onto the area of the substrate excluding the depression; and
    joining the substrate to a wiring-side substrate with the adhesive, the wiring-side substrate having a conductive pattern provided thereon with a varying thickness.

8. The method of manufacturing a light emission detection device according to claim 7, wherein the light-shielding film is a chromium metal film, and the light-transmissive substrate is made of an inorganic glass material.

9. The method of manufacturing a light emission detection device according to claim 8,
    wherein the etching is performed in a wet manner, and
    wherein the method further comprises removing part of the chromium metal film projecting over the depression by applying ultrasonic waves after the etching.

* * * * *